US006106843A

United States Patent [19]
Muthukumarappa et al.

[11] Patent Number: 6,106,843
[45] Date of Patent: Aug. 22, 2000

[54] PROCESS FOR THE ISOLATION OF A NONTOXINOGENIC VIBRIO CHOLERAE STRAIN AND A PROCESS FOR PREPARING CHOLERA VACCINE FROM SAID *VIBRIO CHOLERAE* STRAIN

[75] Inventors: Thungapathra Muthukumarappa; Amit Ghosh; Charu Sharma; Naveen Gupta, all of Union Territory; Asish Mukhopadhyay, Calcutta; Hemanta Kole, Calcutta; Gopinath Balakrish Nair, Calcutta; Ranajit Kumar Ghosh, Calcutta, all of India

[73] Assignees: Council of Scientific & Industrial Research, New Delhi; National Institute of Cholera and Enteric Diseases, Calcutta; Department of Biotechnology, New Delhi, all of India

[21] Appl. No.: 09/243,810

[22] Filed: Feb. 3, 1999

Related U.S. Application Data

[62] Division of application No. 08/988,162, Dec. 10, 1997.

[30] Foreign Application Priority Data

Dec. 10, 1996 [IN] India ............................. 2740/DEL/96
Dec. 10, 1996 [IN] India ............................. 2734/DEL/96

[51] Int. Cl.[7] ..................... A61K 29/106; C07H 21/04; C07K 14/28; C12N 1/21

[52] U.S. Cl. ..................... 424/261.1; 424/234.1; 424/93.4; 424/93.2; 435/252.21; 435/252.3; 435/172.3; 435/248; 435/909

[58] Field of Search ............................. 424/261.1, 234.1, 424/93.4, 93.2; 435/252.1, 252.3, 172.3, 248, 909

[56] References Cited

U.S. PATENT DOCUMENTS

| 4,264,737 | 4/1981 | Murphy | 435/172 |
| 4,882,278 | 11/1989 | Mekalanos | 435/172.3 |
| 5,399,494 | 3/1995 | Kaper et al. | 435/172.3 |
| 5,631,010 | 5/1997 | Mekalanos | 424/235.1 |

OTHER PUBLICATIONS

Dasgupta et al. Vaccine, vol. 12, No. 4, 1995, p. 359–364.

*Primary Examiner*—Phuong T. Bui
*Attorney, Agent, or Firm*—Birch, Stewart, Kolasch & Birch, LLP

[57] ABSTRACT

A process for the isolation of nontoxinogenic *V. cholerae* strain and a process for preparing a cholera vaccine from said *V. cholerae* strain, said process comprising (a) isolating *V. cholerae* from the stool of a patient suffering from cholera by spreading the stool on a selector medium specific for *V. cholerae*, (b) separating the non-toxinogenic *V. cholerae* strain from the population of the *V. cholerae* strains isolated in step (a), and (c) incorporating immunogenic cholera toxin (ctx) B subunit gene into the chromosome of the strain by conventional methods to produce the vaccine.

7 Claims, No Drawings

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer CT1

<400> SEQUENCE: 1
ttagtgttcg atacctttgc a                                              21

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide Primer CT2

<400> SEQUENCE: 2
ttaggcaaaa cggttgcttc ttctcatcat c                                   31

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide Primer CT3

<400> SEQUENCE: 3
ccattgttta acagaaaaat aattgatcaa aac                                 33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide Primer CT4

<400> SEQUENCE: 4
ggaattaagg atgaattatg attaaattaa aa                                  32

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Primer HA1

<400> SEQUENCE: 5
ttcacagagt cagtgaggtt tatatgc                                        27

<210> SEQ ID NO 6
<211> LENGTH: 27
<212> TYPE: DNA
<213> ORGANISM: Artificial Sequence
<220> FEATURE:

```
<223> OTHER INFORMATION: Description of Artificial Sequence:
      Oligonucleotide Primer HA2

<400> SEQUENCE: 6
ttcgctgtag acattggtca attcatc                                            27
```

PROCESS FOR THE ISOLATION OF A NONTOXINOGENIC VIBRIO CHOLERAE STRAIN AND A PROCESS FOR PREPARING CHOLERA VACCINE FROM SAID *VIBRIO CHOLERAE* STRAIN

This application is a divisional of copending application Ser. No. 08/988,162, filed on Dec. 10, 1997, the entire contents of which are hereby incorporated by reference.

FIELD OF THE INVENTION

The present invention relates to a process for the isolation of a non-toxinogenic *Vibro cholerae* strain and its use in the preparation of cholera vaccine. The present invention also, particularly, relates to a process for the preparation of cholera vaccine using *V. cholerae* strain having ATCC Accession No. 202010. The vaccine prepared by the process of the invention has proved efficacious in animal trials. If proved successful in human trials, it can be used to control the disease cholera, since an effective and safe cholera vaccine is still not available. The present invention specifically relates to a process for the preparation of cholera vaccine using *V. cholerae* strain having the ATCC Accession No. 202010 as a parent strain.

The various scientific terms used in this specification are described in alphabetical order as given below:

Annealing refers to the process in which single strands of deoxyribonucleic acid (DNA) having complementary base sequences become paired to form a double stranded molecule.

Clone refers to a large number of cells or plasmid molecules derived from a single ancestral cell or plasmid molecule and a colony refers to a visible cluster of cells formed on a solid growth medium by repeated division of a single parental cell.

Cloning in recombinant DNA technology refers to the linking of a specific gene or DNA fragment to a replicable DNA molecule such as a plasmid or phage DNA.

Colony refers to a visible cluster of cells formed on a solid growth medium by repeated division of a single parental cell.

Colonization refers to the ability of a bacterium to remain at a particular site and multiply.

Denaturation refers to conversion of DNA from double stranded molecule into the single stranded form.

DNA refers to the macromolecule, deoxyribonucleic acid formed from covalently linked deoxynucleotide units.

DNA ligase is an enzyme that joins two DNA molecules through a phosphodiester bond.

DNA polymerase is an enzyme that catalyses the synthesis of DNA from deoxynucleotides under the direction of a DNA template strand.

DNA sequencing refers to determination of the order of nucleotides in a DNA molecule.

Electrophoresis is a technique used to separate molecules on the basis of their different migration rates (due to their molecular size difference) in a solid support in response to an applied electric field.

Electroporation refers to the introduction of DNA molecules into a cell by means of an electric field.

Enterotoxin refers to a protein toxin secreted by bacteria that acts specifically on the intestinal mucosa.

Gene refers to the hereditary unit containing genetic information that is transcribed into ribonucleic acid (RNA) which is processed and either functions directly or is translated into a polypeptide chain.

Genome refers to the total genetic information carried by a cell.

Homologous recombination refers to genetic exchange between identical DNA sequences.

Hybridization refers to the process whereby two complementary nucleic acid strands form a double helix during an annealing period; a powerful technique for detecting specific nucleotide sequences.

Immunity refers to the resistance of an organism to disease causing agents.

Immunogen is an antigen that induces an immune response. oligonucleotide refers to a short single stranded nucleic acid.

Operon refers to a group of contiguous genes that are transcribed into a single messenger ribonucleic acid (mRNA) molecule from a single promoter.

Plasmid is an extra chromosomal genetic element that replicates independently of the host chromosome; used as cloning vector.

Polymerase chain reaction is a technique for amplifying specific regions of DNA by multiple cycles of polymerization, each followed by a brief heat treatment to separate complementary strands.

Primer refers to an oligonucleotide that can hybridize with a longer DNA strand and can be extended by DNA polymerase for example in polymerase chain reaction.

Probe refers to a radioactive DNA molecule used in DNA-DNA hybridization assay.

Promoter refers to a specific DNA sequence at which RNA polymerase binds and initiates transcription.

Protein refers to the linear polymer of amino acids linked together by peptide bonds in a specific sequence.

Recombinant DNA technology refers to procedures for creating new DNA molecule by joining DNA segments from different DNA molecules.

Recombination is a process in which chromosomes or DNA molecules are broken and then rejoined in new combination.

Restriction enzyme is a nuclease that recognizes a short nucleotide sequence (restriction site) in a DNA molecule and cleaves the molecule at that site.

Ribosome binding site or Shine Dalgarno sequence is the base sequence in a prokaryotic mRNA molecule to which a ribosome binds to initiate protein synthesis.

Selection refers to a procedure designed in such a way that only a desired type of cell can survive (as in selection for resistance to an antibiotic).

Southern hybridization is a process in which following electrophoretic separation of nucleic acids, denatured DNA is transferred from gel to a membrane filter and then exposed to radioactive DNA probe under conditions of renaturation. The radioactive regions indicate the DNA segments homologous to the probe.

Start codon refers to the triplet sequence AUG on the mRNA molecule from which translation into the polypeptide chain starts.

Sticky end refers to a single stranded region at the end of a double stranded DNA molecule that is complementary to a single stranded region at the other end of the same molecule or at the end of a different molecule.

Stop codon refers to one of the three mRNA codons: UGG, UAA, or UGA, at which polypeptide synthesis stops.

Subunit refers to a polypeptide chain that is part of a protein containing several polypeptide chains.

Suicide vector refers to the plasmid vector which cannot replicate in a host cell that which does not provide the necessary components for its replication.

Tandem duplication refers to repetition of a DNA segment on a chromosome in a contiguous array in the same orientation.

Template refers to a nucleic acid strand whose base sequence is copied during a polymerase chain reaction.

Transcription refers to the process by which the information contained in the coding strand of DNA is copied into a single stranded DNA molecule of a complementary base sequence.

Transcription activator is a positive control element that stimulates transcription by binding to particular sites in DNA.

Transcription terminator is a sequence of DNA, represented at the end of RNA transcript that causes RNA polymerase to terminate transcription.

Transcription start site is the codon from which DNA is transcribed to RNA molecule.

Transformation refers to introduction of DNA into a bacterial cell.

Translation refers to the process by which the amino acid sequence of a polypeptide chain is derived from the nucleotide sequence of a mRNA molecule associated with a ribosome.

Vector refers to a plasmid cloning vehicle through which a DNA segment can be carried from one organism to another.

Cholera is a lethal diarrheal disease caused by the gram negative bacterium *Vibrio cholerae* (*V. cholerae*). This disease, which has killed millions of people, continues to be a major health hazard worldwide affecting about one-half million people every year. Today almost every country in the world is affected by it. Furthermore, according to World Health Organization (WHO), even Europe, which had been reporting only imported cases of cholera, registered a 30 fold increase in indigenous cholera cases in 1994.

The severe diarrhea that occurs during cholera disease is the result of a host reaction to an extracellular enterotoxin known as cholera toxin. The cholera toxin consists of two different protein subunits which are encoded by the genes ctxA and ctxB. These genes form a single operon called ctx AB (or the ctx operon). A single A subunit and five B subunits make up the complete toxin molecule. It is the A subunit of the cholera toxin which is responsible for the fluid loss characterized by the disease by upsetting the fine control of water and electrolyte balance of the intestinal epithelial cells. The B subunits bind to the host intestinal membrane and perhaps aid the entry of the catalytic A subunit into the host mucosal cells. The B subunit is also immunogenic and is capable of eliciting antitoxic immunity in the host.

PRIOR ART REFERENCES

In order to control or prevent cholera, various vaccines have been developed. A whole cell killed vaccine administered parenterally is still being used in developing countries but offers only about 50% protection, and is effective for only a few months. [(i) Fellay, J. C. and Gangarosa (1978) in Cholera and Related Diarrheas (Ouchterlony, O. & Holmgren J. eds.) 43$^{rd}$ Nobel Symp. Stockholm pp 204–210, Karger, Basel. (ii) Svennerholm, A. M., Helmgren, J., Hanson, L. A., Lindblad, B. A. Quereshi, F. and Rahimtoola, R. J. (1977) Scand J. Immunol 6,1345–1349. (iii) Svennerholm, A. M., Hanson, L. A., Holmgren J., Lindblad, B. S., Nilsson, and Quereshi, F. (1980) Infect Immun 30, 427–430]. After the advent of recombinant DNA technology, attenuated live oral *Vibrio cholerae* strains lacking cholera toxin A subunit turned out to be attractive candidates since they would mimic infection derived immunity by colonizing the intestine and stimulate both antibacterial and antitoxic immunity. [(i) Kaper, J. B., Lockman, H., Baldini, M. M. and Levine, M. M. (1984) Nature 308,655–658. (ii) Kaper, J. B., Lockman , H., Baldini, M. M. and Levine, M. M. (1984) Biotechnology 2, 345–349. (iii) Mekalanos, J. J., Swartz, S. J., Pearson, G. D. N., Harford, N., Groyne, F. and M. de Wilde (1983) Nature 306, 551–557]. But all such attenuated *Vibrio cholerae* 01 vaccine strains developed so far have still been found to cause mild to moderate diarrhea when tested on volunteers. [(i) Levine, M. M., Kaper, J. B., Herrington, D. A., Losonsky, G., Morris, J. G. Clements, M. L., Black, R. E., Tall, B. and Hall, R. (1988) Infect Immun 56, 161–167._(ii)Herrington, D., Hall, R., Losonsky, G., Mekalonos, J. J., Taylor, R. K. and Levine, M. M. (1988) J Exp Med 168, 1487–1492]. It was subsequently discovered that virulent strains of *V. cholerae* possess genes for other toxins besides the cholera toxin. It was further discovered that ctxAB genes are actually a part of a virulence cassette which encodes four other virulence genes namely zot, ace, cep and orfU besides the ctx. The genes encoding all these factors reside in a mobile genetic element. Within this element all of the above genes are present as a contiguous array in what is known as the core element. The core element is flanked on both sides by a 2.7 kb repetitive sequence called a RS1 element. The RS1 element encodes a site specific recombination system which is responsible for the recombinase A independent integration, duplication and amplification of the toxin cassette. Utilizing this knowledge, attempts were made to create a vaccine strain in which all of these virulence genes ctxA, zot, ace, etc., were deleted. [Michalski, J., Galen, J. E., Fasano, A., and Kaper, J. B. (1993) Infect Immun 61, 4462–4468]. However, when such a strain was tested, it was found to be equally reactogenic as other vaccine prototypes which were not devoid of zot, ace etc., virulence genes [Tacket, C. O., Losonsky, G., Nataro, J. P., Cryz, S. J., Edelman, R., Fasano, A., Michalski, J., Kaper, J. B. and Levine, M. M. (1993) J. Infect Dis 168 1536–1540].

Recently, the applicants have come across two South African Patent Nos. 93/4736 and 95/0082 relating to cholera vaccine. The starting strains described in the South African Patent are:

1. Peru-2
2. Bang-2
3. Bah-2
4. Bengal-2

Nos. 1–3 are described in Taylor et al (1994) J. Infect Diseases 170, 1518–23. These are NOT natural isolates but are genetically engineered strains to produce ctx. South African patents describe development of Soft Agar Penetration defective mutants from these.

No.4 is described in Waldor & Mekalanos (1994) J. Infect. Diseases, 170, 278 Bengal-2 is genetically engineered construct and NOT a natural ctx from *V. Cholerae* M020 is a *V. cholerea* 0139 strain. South African Patents describe development of Soft Agar Penetration defective mutant from this.

On the other hand, the starting strain of the present invention is a naturally occuring ctx ace zot strain. This was engineered to create the vaccine strain which has been deposited at American Type Culture Collection, 12301 Parklawn Drive, Rockville, Md. 20852 USA and has been assigned the Accession No. 202011 which produces only the immunogenic "B" subunit of the cholera toxin.

Despite the good protection offered by the various vaccine candidates developed by such "deletional" approaches, their main drawback was that all of them were capable of causing mild to moderate diarrhea. The reactogenicity of these earlier vaccine candidates was probably dependent to a large extent on unknown factors present in the parent strains. To circumvent this problem during developing an ideal cholera vaccine which is safe (i.e. non-reactogenic) and highly protective, an alternative approach would be to develop a vaccine from a strain which is non-toxinogenic in biological assays and is devoid of all known virulence genes.

OBJECTS OF THE INVENTION

Thus, the main objective of the present invention is to provide a process for the preparation of cholera vaccine.

Another objective of the present invention is to provide a process for the preparation of cholera vaccine using a non-toxinogenic strain of *Vibrio cholerae* having ATCC Accession No. 202010.

Yet another object of the invention relates to producing a chlorea vaccine having ATCC Accession No. 202011 which has been constructed by incorporating the immunogenic ctxB subunit gene into the chromosome of the nontoxinogenic *V. chloreae* strain having ATCC Accession No. 202010.

SUMMARY OF THE INVENTION

Accordingly, in the present invention, there is provided a process for the isolation of a strain of *V. chloerae* having ATCC Accession No. 202010 and a process for the preparation of a cholera vaccine useful for preventing cholera which comprises:

a. isolating *V. cholerae* from the stool of a patient suffering from cholera by spreading the stool on a selector medium specific for *V. cholerae*.

b. Separating the non-toxinogenic *V. cholerae* strain from the population of the strains isolated; the strain having the ATCC Accession No. 202010, and c. Incorporating immunogenic cholera toxin (ctx) B subunit gene into the chromosome of the strain having the ATCC Accession No. 202010 by conventional methods to produce the vaccine.

DETAILED DESCRIPTION OF THE INVENTION

The main finding of the present invention is the integration of the immunogenic B Subunit gene of the cholera toxin into the chromosome of the non-toxinogenic strain of *V. cholerae* by targeted genetic recombination at the hemolysinA gene (hlyA) which results in the disruption of hlyA. The present invention is derived from a strain of *V. cholerae* of 01 serotype which is non-toxinogenic, devoid of known virulence genes and is a good colonizer. The strain is a clinical isolate recovered from a patient with cholera and is identified as *Vibrio cholerae* of the 01 serogroup, Inaba serotype and belonged to the Eltor biotype. This strain is selected after screening several hundred strains of *V. cholerae* using a battery of DNA probes specific for virulence associated factors including cholera toxin, zonula occludens toxin, accessory cholera enterotoxin. This strain does not possess the virulence package normally located on a 4.5 kb region in toxinogenic strains and therefore does not produce cholera toxin or the other known secondary toxins which reportedly exacerbate the fluid accumulation. This strain, however, has the E1 Tor hemolysin A gene, which would be a suitable target on the chromosome for the integration of the immunogenic ctxB subunit gene to make it a producer of the B subunit of cholera toxin. This strain also has the toxin coregulated pilus A (tcpA) gene which is required for colonization of the strain in the intestine, and the toxR gene which is required for promoting the expression of the ctxB subunit gene. The reasons for selecting the strain having the ATCC Accession No. 202010 as a starting strain for developing an oral recombinant vaccine are as follows:

1. The strain having ATCC Accession No. 202010 is not capable of accumulating fluid in the ligated ileal loop rabbit model indicating that the strain does not produce any secretogenic factors.
2. The strain does not produce any adverse effect on rabbits when examined by the RITARD model; hence the strain is not reactogenic.
3. Despite non-reactogenicity, this strain displays impressive colonization ability in the rabbit model and this is probably due to the presence of the toxin coregulated pilus whose presence was determined directly by Southern hybridization studies, an important factor assisting colonization of *Vibrio cholerae*. It has been found that when the ctxB gene is introduced with its own promoter and its own Shine Dalgarno sequence into the chromosome of this strain, it ensures optimum expression of the gene in the gut. It has also been found that the recombinant *V. cholerae* clones thus created show up as an efficacious vaccine in animal model studies.

The detailed procedure of this invention are given below:

Isolation of the parent *V. cholerae* strain having ATCC Accession No. 202010,

Stool specimens from cholera patents were collected in sterile MacCartney bottles with sterile catheters. Soon after collection stool specimens were transported to the laboratory and examined within 2 hours for *V. cholerae* and for other common toxinogenic enteropathogens such as enterotoxinogenic *E. coli* (ETEC), Shigella, Salmonella and Campylobacter spp. by standard published techniques (W.H.O Program for control of diarrheal diseases (CCD/83.3 Rev.1), Manual for laboratory investigations of acture enteric infections, Geneva, W.H.O., 1987).

*V. cholerae* strains from the stool specimens were isolated by plating the stool specimens on a selective medium like thiosulfate-citrate bile salts sucrose agar (TCBS), tellurite taurocholate gelatin agar (TTGA), Vibrio agar, sucrose tellurite teepol medium and polymyxin mannose tellurite agar which are specific for *V. cholerae*. The *V. cholerae* strains that had grown as colonies were collected manually. Several hundred strains so obtained were grown in media specific for identification of *V. cholerae* by biochemical tests. The several hundred strains that were confirmed to be *V. cholerae* 01 (of serotype) were grown as individual colonies on Luria broth agar for screening by hybrididization with DNA probes specific for toxin genes ctx, zot and ace. The colony hybridization experiments were performed by known methods. The strains that were found to be devoid of the toxin genes vis, ctx, zot, ace were tested for cholera toxin like and other cytotoxin activities by known methods (Oku Y, Uesake Y, Hirayama T, Takeda Y. Microbial Immunol 1988:32:807–816 and Nair G. B., Olku Y, Takeda Y. et al. Appl. Environ. Microbiol 1988; 54: 3180–3182).

One of the strains did not have the toxin genes and did not have cholera toxin or other cytotoxin activities. This *V. cholerae* is the strain having the ATCC Accession No. 202010. In this strain the presence of the cryptic hemolysin A gene was confirmed by hybridization with hlyA probe. This is essential since the integration of ctxB subunit gene for the preparation of cholera vaccine has to be carried out by targeted recombination at hlyA locus. Since the product of tcpA gene is the main component of the pilus required for effective colonization of *Vibrio cholerae* in the intestine, its presence was also confirmed with tcpA probe. Further, since the transcriptional activator ToxR is required for the optimal expression of genes under the control of ctx promoter, the presence of toxR gene was determined by hybridization with the toxR probe.

The *V. cholerae* strain ATCC 202010 was tested in a ligated ileal loop assay as described by De S. N. in Nature 183, 1533–1534 (1949) and Formal et al in Br. J. Exp. Pathol. 42, 504–510 (1961). The strain was not capable of accumulating fluid in the ligated ileal loop rabbit model indicating that the strain does not produce any secretogenic factors.

The strain did not produce any adverse effect on rabbits when examined by the RITARD model following conventional methods showing that the strain is nonreactogenic. Despite non-reactogenicity, this strain displayed impressive colonization ability as determined by conventional method, which is required of the strain to function as effective vaccine.

The *V. cholerae* strain having the Accession No. ATCC 202010 can be grown in Luria broth at 30–37° C. temperature and stored in the same medium with 20% (vol/vol) glycerol at −60° C. to −80° C.

To facilitate the preparation of the vaccine using the parent strain of *V. cholerae* having ATCC Accession No. 202010, a series of genetic manipulations leading to the construction of ctx subunit gene flanked by hlyA gene sequences was carried out. These steps are given below:

(i) Creation of a construct of a ctxB subunit gene with its own Shine-Delgarno sequence and the promoter of a ctx operon by first cloning the cholera toxin (ctx) operon from the chromosome of *V. cholerae* 569B strain (National Institute of Cholera and Enteric Diseases) and then deleting the ctxA subunit gene from the cloned operon by inverse PCR.

(ii) Cloning of the target locus hemolysinA gene (hlyA) for the purpose of targeted recombination.

(iii) Disrupting the hlyA gene sequence with the ctxB subunit gene construct obtained at step (i)

(iv) Cloning the disrupted hlyA construct that has the ctxB subunit gene into the suicide plasmid vector.

(v) Mobilization of the suicide vector bearing the disrupted hlyA construct into the parent strain by conjugation, in order to allow targeted integration of the ctxB gene construct at the hlyA gene.

(vi) Identification of the recombinant *V. cholerae* clones with the integrated ctxB gene by Southern hybridization and polymerase chain reaction.

The first step among the manipulations was to clone the ctx operon of known *Vibrio cholerae*. The ctx operon of known *Vibrio cholerae* 01 strain 569B was cloned after its amplification from the genome by polymerase chain reaction. In the polymerase chain reaction, *Vibrio cholerae* 569B chromosomal DNA was used as the template to amplify the ctx operon with the primers CT1 (SEQ ID NO: 1) and CT2 (SEQ ID NO: 2). oligonucleotide CT1 is complementary to the chromosomal DNA sequence located 149–172 nucleotides upstream of the transcription start site of ctx operon. Oligonucleotide CT2 is complementary to the chromosomal DNA sequence located 43–67 nucleotides downstream of the stop codon of ctx. When these two oligonucleotides are used as primers to amplify the DNA sequence, the product obtained is the complete ctx operon consisting of the genes encoding the cholera toxin A and B subunits along with the promoter and the upstream ToxR binding repeats at the 5' end, and the transcription termination signal at the 3' end of the operon.

In the polymerase chain reaction, following an initial denaturation step, the reaction was cycled about 30 times through a denaturation step, an annealing step and an extension step. At the end of the last cycle, an additional extension step was included. After the polymerase chain reaction, the reaction mix was extracted with equal volume of 50:50 mixture of phenol:chloroform. The aqueous phase was passed through Sephadex G50 spin column to remove free nucleotides and precipitated by ethanol. After resuspending the DNA, it was treated with T4 DNA polymerase enzyme in the presence of dTTP. This resulted in the amplified DNA product with 5' TT-dinucleotide overhangs.

To clone the amplified DNA that was modified as above, the plasmid vector pBS+ was first linearized with the restriction enzyme, EcoRI. It was then treated with the Klenow fragment of *E. coli* DNA polymerase I in presence of dATP. This treatment resulted in 5' AA overhangs at both the ends of the linearized pBS+ vector DNA. This vector DNA preparation was ligated to the amplified ctx operon with 5' TT-overhangs at 1:2 molar ratio by T4 DNA ligase. After this dinucleotide sticky end ligation, the reaction mix was used to transform *E. coli* "Sure" strain by electroporation.

The resulting recombinant plasmid clones were analyzed by restriction enzymes for which the sites on the ctx operon were known (e.g. Nde I, XbaI, ClaI). The insert of one clone called pGT1 has the complete ctx operon as confirmed by restriction analysis and sequencing. The nucleotide sequence was determined to rule out the possibility of any error introduced during the polymerase chain reaction. The plasmid clone pGT1 was found to contain the complete ctx operon consisting of the genes encoding cholera toxin A and B subunits along with the promoter and the upstream ToxR binding repeats at the 5' end and the transcription termination signal at the 3' end of the operon.

In the next step, deletion of complete ctx-A coding sequence from the plasmid clone pGT1 was achieved by inverse polymerase chain reaction. Inverse PCR utilizes oligonucleotide primers that diverge from each other and amplify the plasmid excluding the ctx-A gene. An inverse polymerase chain reaction was carried out using phosphorylated oligonucleotides CT3 and CT4 as primers and the plasmid pGT1 as the template DNA. The resulting amplified product was phenolysed, passed through Sephadex G-50 spin column to remove the free nucleotides, and ethanol precipitated. It was then treated with T4 DNA polymerase in presence of dTTP to generate 5' GG-overhang at the terminus corresponding to CT3 and 5' CC-overhang at the terminus corresponding to CT4. Ligation of the above dinucleotide overhangs, was carried out by T4 DNA ligase. The ligation product was used to transform *E. coli* "Sure" strain by electroporation. The recircularization of the inverse polymerase chain reaction product resulted in the fusion of the ctx promoter and the ctx B subunit gene. This construct ctx Promoter-B was identified in the various plasmid clones by a polymerase chain reaction using the CT1 and CT2 primers as explained before, which yield a 0.63 kilobase fragment corresponding to the ctx promoter-B construct. In this ctx promoter-B construct, the ctxB subunit gene is under the control of ctx operon promoter but its translation is initiated by its own Shine-Delgarno sequence. The expression of the B subunit from the various clones was confirmed by a Bead ELISA assay. The nucleotide sequence of the ctx-Promoter-B construct of one plasmid clone pGT 3.1 was determined in order to confirm the presence of the promoter-B subunit gene fusion point. The ctx Promoter-B gene construct from pGT3.1 was used in a latter step to disrupt cloned hlyA gene.

Since it was decided to introduce the ctx Promoter-B gene construct into the *Vibrio cholerae* strain having the ATCC Accession No. 202010 by targeted recombination at the hlyA gene, it was essential to make a construct in which the cloned hlyA gene sequence is disrupted in the middle by the ctx Promoter-B construct. For this purpose it was necessary to clone the hlyA gene of *V. cholerae*. A partial A gene sequence which lacks the 5' flanking region and a large part of the coding region at the 3' side was cloned after its amplification via PCR from the *Vibiro cholerae* genome. The size of the complete coding region of hlyA gene is about 2.2 kilobases out of which 1.7 kilobases of the hlyA gene were amplified from the genomic DNA of *V. cholerae* of 01 serotype strain. The polymerase chain reaction consisted of an initial denaturation step, and several cycles of denaturation, annealing and extension . An additional extension step was included (at the end of the last cycle). The polymerase chain reaction product was analysed by agarose gel electrophoresis for the presence of a 1.7 kilobase DNA fragment. The reaction product was phenolyzed, passed through Sephadex G-50 spin column to remove free nucleotides, and ethanol precipitated. The purified DNA was treated with T4 DNA polymerase in the presence of dGTP to generate 5' TT-overhangs.

To clone the amplified hlyA gene sequence with the modified termini as described above, the plasmid vector pUC9 was first linearized with the restriction enzyme EcoRI. The linearized pUC9 DNA was then treated with Klenow fragment of *E. coli* DNA polymerase I in presence of dATP to generate terminal 5' AA-overhangs. This vector DNA preparation was ligated to the amplified hlyA gene sequence with 5' TT overhangs by T4 DNA ligase. After this ligation reaction, the reaction mix was used to transform *E. coli* "Sure" strain by electroporation. The resulting plasmid clones were analyzsed by digestion with appropriate restriction endonucleases. One of the plasmid clones pGT89 which had the 1.7 kilobase hlyA insert was used in the subsequent step to disrupt the hlyA sequence by the ctx promoter-B gene construct.

In the next step, the ctx Promoter-B construct of pGT 3.1 was amplified using oligonucleotide primers CT1 and CT2. The amplified product was phenolyzed, passed through Sephadex G50 spin column and ethanol precipitated. The purified ctx Promoter-B construct fragment was treated with T4 DNA polymerase in presence of dTTP to generate 5' terminal TT-overhangs. The ctx Promoter-B construct with 5' TT-overhangs was inserted into the middle of the cloned hlyA gene sequence in place of the 0.4 kilobase HpaI fragment. Since the plasmid vector pUC9 does not have a site for HpaI enzyme, digestion of pGT89 with HpaI would result in a 0.4 kilobase fragment from the middle of the cloned hlyA gene sequence and a 3.9 kilobase fragment. Plasmid pGT89 was digested with HpaI enzyme and the DNA fragments were separated by agarose gel electrophoresis. The 3.9 kilobase HpaI fragment was electroeluted and purified. It was then treated with T4 DNA polymerase in the presence of dGTP to generate 5' terminal AA-overhangs. The 3.9 kilobase fragment with 5' AA-overhangs was ligated to the ctx Pr-B construct with 5' TT-overhangs by T4 DNA ligase. The ligated mix was used to transform *E. coli* "Sure" strain by electroporation. The recombinant plasmid clones were identified by colony hybridization using a ctx Promoter-B construct probe. Digestion of the recombinant plasmids with EcoRI enzyme gave an 1.9 kilobase insert of hlyA gene sequence disrupted in the middle by the ctx Promoter-B construct. The EcoRI insert from one recombinant plasmid pGT39 was used for cloning the insert into the suicide vector pGP704 (Miller V. L. and J. J. Mekalanos (1988) J. Bac 170; 2575–2583).

In the next step, the ctx promoter-B construct along with the flanking hlyA sequences were cloned into the plasmid suicide vector. The plasmid suicide vector pGP704 was digested with EcoRI enzyme, and subsequently the 5' phosphate groups of the linearized vector were removed by treatment with calf intestinal phosphatase. The EcoRI digested, dephosphorylated pGP704 was electrophoresed on a 0.8% agarose gel and the corresponding DNA band was electroeluted and purified. This was done to confirm that no trace of the undigested vector DNA was present in the vector DNA preparation. The vector was then ligated to the 1.9 kilobase EcoRI insert of pGT39 at 1:5 molar ratio by T4 DNA ligase, and the ligated mix was used to transform *E. coli* SM10 pir strain by electroporation. The recombinant plasmid clones were identified by colony hybridization, using a ctx Promoter-B construct probe. Digestion of the recombinant plasmid with EcoRI gave a 1.9 kilobase insert which represented the cloned hlyA gene sequence disrupted by the ctx Promoter-B construct. One of the clones pGT27 was used for mobilization into the *V. cholerae* strain having ATCC Accession No. 202010 for integration at the hlyA gene.

In the following step, mobilization of pGT27 into *V. cholerae* 01 strain having ATCC Accession No. 202010 was achieved by conjugation between the *Vibrio cholerae* having ATCC Accession No. 202010 strain and the *E. coli* strain SM10 pir containing the plasmid pGT27. The plasmid clone pGT27 in the *E. coli* host strain SM10 pir and the *V. cholerae* strain having ATCC Accession No. 202010 were grown in LB to midlog phase without shaking. A small quantity of the donor strain, i.e., SM10 pir strain with pGT27 and an equal quantity of the recipient strain, i.e., *V. cholerae* having ATCC Accession No. 202010 strain were mixed in 1.5 ml microfuge tubes and briefly centrifuged to collect the cells. After removing the supernatant, Luria broth was added to the cell pellet and the cells were suspended in it by pipetting up and down. The cell suspension was then spotted on a 0.4 mm membrane disc placed on the surface of a LB agar medium. The suspension was absorbed on the membrane. The donor and the recipient cells on the membrane were allowed to mate for about 4–9 hours at 37° C. The membrane filter was then collected into a tube, and 1 ml of Luria broth was added. The cells on the membrane were resuspended in the medium by vortexing briefly. The suspension so obtained was spread on LB agar medium containing 10 μg/ml of streptomycin sulfate and an appropriate concentration of ampicillin, to select only the recombinant *V. cholerae* having ATCC Accession No. 202010 clones which had the plasmid pGT27 integrated into their genome. (The ampicillin resistance is conferred by the suicide plasmid vector). When the sensitivity of the parent *V. cholerae* having ATCC Accession No. 202010 strain to ampicillin was checked, it was found that an ampicillin concentration as low as 5 μg/ml, could completely inhibit its growth on LB agar medium. Therefore selection of recombinant clones in which pGT27 was integrated, was performed on LB plates containing 10 μg/ml of streptomycin sulfate and 10–100 μg/ml of ampicillin.

The recombinant *V. cholerae* clones were identified by colony hybridization. Next, positive colonies were analyzed by colony hybridization with the ctx B gene sequence as the probe. Since the recipient *V. cholerae* having ATCC Accession No. 202010 does not possess the ctx operon and the ctx Promoter-B construct was introduced through pGT27, only the recombinant *V. cholerae* clones in which the pGT27 was integrated are expected to hybridize with the ctx B gene probe. Results showed that all of the ampicillin resistant colonies hybridized to the ctx B probe. From several colonies, chromosomal DNA was isolated and used as template DNA in separate polymerase chain reactions with the hlyA specific primers HA1 and HA2. These two primers define a 1.7 kilobase sequence from the wild type hlyA gene and 1.9 kilobase sequence from pGT27, in which the hlyA gene sequence is disrupted by ctx Promoter-B construct. When *V. cholerae* having ATCC Accession No. 202010 chromosomal DNA is used as a template, these primers will amplify only the 1.7 kilobase sequence, whereas when the chromosomal DNA of recombinant *V. cholerae* is used as a template, these primers will amplify, in addition, a 1.9 kilobase fragment. In all of the clones tested by polymerase chain reaction, both of the above mentioned fragments were amplified by the primers HA1 and HA2. The expression of ctxB subunit from these clones was analyzed by bead ELISA, as described in the article "Detection of cholera toxin by a highly sensitive bead-Enzyme Linked Immunosorbent Assay" by Yoshihiko Uesaka, Yoko Otsuka, MiksuakiKahida, Yuichi Oku, Kazuki Horigome, G. Balakrish Nair, S. C. Pal, Shinji Yamasaki and Yoshifumi Takeda in Microbiol. Immunology, Vol. 36 (1), 43–53 (1992).

In order to perform genomic Southern hybridization, genomic DNA isolated from the recombinant *V. cholerae* clones was digested with XbaI, SalI and HpaI separately. The DNA fragments of individual restriction digestions were separated by electrophoresis on agarose gel and transferred and immobilized onto a nylon membrane by Southern transfer. The immobilized DNA was hybridized with ctx B gene probe and hlyA probe in separate experiments. The analysis of the genomic Southern hybridization results revealed that pGT27 was indeed integrated at the hlyA gene of *V. cholerae* having ATCC Accession No. 202010. It was also revealed that pGT27 was repeated in tandem in several recombinant clones. One of the clones was chosen as a vaccine strain and tested in animal models. The cholera vaccine strain has been deposited and given the ATCC Accession No. 202011. The strain can be grown in Luria broth medium at 30–37° C. temperature and stored in the same medium with 20% (vol/vol) glycerol at −80 to −60° C. The ability to produce the B subunit of cholera toxin by the vaccine strain of the ATCC Accession No. 202011 was monitored using the bead-ELISA by Yoshihiko Uesaka, Yoko Otsuka, Miksuaki Kahida, Yuichi Oku, Kazuki Horigome, G. Balakrish Nair, S. C. Pal, Shinji Yamasaki and Yoshifumi Takeda in Microbiol. Immunology, Vol. 36(1), 43–53 (1992). The parent strain did not produce B subunit whereas the vaccine strain showed copious production of the B subunit, as measured by optical density, because the former strain has multiple copies of CT-B as compared to the latter, which only has a single copy.

Having determined that the genetic manipulations were appropriately done, the next effort made was to determine whether the vaccine induced fluid accumulation in the ligated rabbit ileal loop assay. Ligated ileal loop assay (rabbit model) was carried out as described in De, S. N., Nature 183, 1533–1534 (1959) and Formal, S. B., Kundel, D., Schneider, H., Kunev, N. and Sprinz, H. Br. J. Exp. Pathol. 42, 504–510 (1961). The vaccine strain having the ATCC Accession No. 202011 did not induce fluid accumulation. This attested to the fact that the vaccine construct produces the B subunit which as expected is inocuous and incapable of inducing fluid accumulation. The next series of experiments were conducted to determine whether the vaccine strain was reactogenic using an in vivo rabbit model. Vaccine trials on rabbits by RITARD model were performed as described by Spira, N. M., Sack, R. B. and Froehlich, J. L. (1981). Infect. Immun, 32, 739–747. It was clear that the vaccine strain having the ATCC Accession No. 202011 did not induce diarrhea when fed orally to rabbits. Based on these results, challenge studies with strains of *V. cholerae* of 01 serotype belonging to both El Tor and classical biotypes were conducted in several batches. The data of the challenged studies in rabbits can be summarized as follows:

1. Rabbits immunized with vaccine strain having the ATCC Accession No.202011 were significantly protected from a challenge with a classical biotype and an ElTor biotype strain. This was evident from the absence of diarrhea in the immunized rabbits while the control rabbits had profound diarrhea.
2. The colonization ability of the challenge strains in the immunized rabbits were significantly lower as compared to the control rabbits.
3. The non-reactogenicity of the vaccine strain having the ATCC Accession No. 202011 was again evident by its inability to provoke diarrhea in the control rabbits.
4. The immunogenicity of the vaccine strain having the ATCC Accession No. 202011 was evident since there was a significant rise in antibody titre against lipopolysaccharide, outer membrane protein, whole cell lysate and cholera toxin in immune sera as compared to the preimmune sera of rabbits orally immunized with the vaccine strain.

All of the experimental procedures described are carried out following standard methods and experimental conditions given below:

*Escherichia coli* and *Vibrio cholerae* strains were grown and maintained in Luria Broth (LB). Where required, appropriate antibiotics were added to the growth medium. Preparation of ampicillin, streptomycin sulfate stocks, LB medium, and other details for handling bacteria were followed from Molecular cloning (1989) by J. Sambrook, E. F. Fritsch and T. Maniatis, Cold Spring Harbor Laboratory.

The polymerase chain reactions were carried out using vent DNA polymerase (exonuclease$^+$) and the basic reaction conditions were 10 mM KCl, 10 mM $(NH_4)_2SO_4$, 20 mM Tris Hcl (pH 8.8), 4 mM $MgSO_4$, 200 $\mu$M each dNTP, 0.1% Triton X-100, 1 $\mu$m primers, 100 ng of chromosomal DNA template or 10–20 ng of plasmid DNA template and 2 units of vent DNA polymerase in a total volume of 100 $\mu$l.

Treatment of DNA with T4 DNA polymerase was carried out in 33 mM Tris acetate (pH 8.0), 66 mM potassium acetate, 10 mM magnesium acetate, 0.5 mM dithiothreitol, 100 $\mu$g/ml bovine serum albumin (BSA), 2 units of T4 DNA polymerase, at 12° C. for 30 minutes in the presence of appropriate dNTP.

Treatment of DNA with Klenow fragment of *E. coli* DNA polymerase I was carried out in 50 mM Tris-cl (pH 7.6), 10 mM $MgCl_2$, 50 $\mu$g/ml BSA and 1 unit of the enzyme at room temperature for 20 minutes, in the presence of appropriate dNTP.

Ligitation of the DNA was carried out in 20 mM Tris-Cl (pH 7.6), 5 mM MgCl$_2$, 5 mM DTT 50 µg/ml BSA, 1.5 unit of T4 DNA ligase and 0.5 mM ATP at 12° C. for 12–16 hours.

Transformation of *E. coli* cells was performed by electroporation using a BIORAD gene pulser. Preparation of *E. coli* cells or electroporation and the electroporation details were followed from manufacturer's instructions.

Dideoxynucleotide sequencing of DNA was performed using the sequence kit obtained from the United States Biochemicals Company, Cleveland, Ohio, USA.

Procedures for isolating plasmid DNA, digestion of DNA with restriction enzymes, agarose gel electrophoresis of DNA, electroelution of DNA fragments, purification of DNA by phenol extraction, spin column chromatography in sephadex G-50 to remove free nucleotides from the polymerase chain reactions, precipitation of DNA with ethanol, radiolabelling of DNA probe, colony hybridization and Southern hybridization protocols are all essentially as described in Molecular cloning (1989) by J. Sambrook, E. F. Fritsch, and T. Maniatis, Cold Spring Harbor. Protocol to isolate genomic DNA from *Vibrio cholerae* was followed from Current Protocols in Molecular Biology by Ausubel et al (1987) Massachusetts General Hospital & Harvard Medical School.

The process of the present invention is illustrated through the examples given below, which should not, however, be construed to limit the scope of the present invention.

EXAMPLE 1

Isolation of the parent *V. cholerae* strain having ATCC Accession No. 202010

Stool specimens from cholera patients were collected immediately on admission to the Infectious Diseases Hospital, Calcutta, in sterile MacCartney bottles with sterile catheters. Soon after collection, stool specimens were transported to the laboratory and examined within 2 hours for *V. cholerae* and for other common toxinogenic enteropathogens such as enterotoxinogenic *E. coli* (ETEC), Shigella, Salmonella and Campylobacter spp. by standard published techniques (World Health Organization. Programme for control of diarrheal diseases [CCD/83.3 Rev.1], Manual for laboratory investigations of acute enteric infections. Geneva, World Health Organization, 1987). To select *V. cholerae* strains in the stool specimens, plates of Thiosulphate-Citrate-Bile Salts-Sucrose Agar (TCBS; Eiken, Japan) were streaked with two or three loopfuls of stool specimens. After incubation overnight at 37° C., colonies from each stool sample showing growth on the selective agar were inoculated on to a multi-test medium (Nair G B, Misra S, Bhadra R K, Pal S C. Appl Environ Microbiol 1987, 53: 1203–1205). Strains that showed typical alkaline slant-acid butt reaction on the multi-test medium were further examined. The oxidase reaction and slide agglutination was performed with polyvalent 01 and monospecific Ogawa-Inaba antisera prepared at the National Institute of Cholera and Enteric Diseases, Calcutta, India. Several hundred strains of *V. cholerae* 01 obtained from above were plated as colonies on Luriabroth agar for screening by hybridization with DNA probes specific for toxin genes ctx, zot and ace. Purified DNA was labelled with $^{32}P$ by incorporating [α-$^{32}P$] dATP to a specific activity of $2\times10^8$–$8\times10^8$ cpm/μg of DNA by nick translation. Radiolabelled probe DNA was purified by chromatography on NACS PREPAC as specified by the manufacturer (Bethesda Research Laboratories, USA). The colony blot was prepared on autoclaved grid nitrocellulose filter (Schleicher and Scheuell Co.; BA 85/20 and hybridization was performed under high stringency as described previously (ref. Karasawa T, Mihara T, Kurazono H et al. to detect distribution of the zot (zonula occludens toxin) gene among strains of *Vibrio cholerae* 01 and non-01. FEMS Microbiol Lett 1993; 106: 143–146).

The strains that were found to be devoid of the toxin genes viz, ctx, zot and ace were tested for cholera toxin-like and other cytotoxin activities. For this purpose, the strains were grown in casaminoacid yeast extract (CAYE) medium supplemented with 90 μg/ml lincomycin, while the culture filtrates were examined for the presence of cholera toxin (T)-like enterotoxin and for theromostable direct haemolysin in a highly sensitive bead-ELISA (ref. Oku Y, Uesaka Y, Hirayama T, Takeda Y. Development of a highly sensitive Bead-ELISA to detect bacterial protein toxins. Microbiol Immumol. 1988; 32: 807–816; Uesaka Y, Otsuka Y, Kashida M et al. Detection of cholera toxin by a highly sensitive bead enzyme linked immunosorbent assay. Microbiol Immunmol 1992; 36: 43–53). Various dilutions of purified CT (Sigma) or the culture filtrate of strain NICED 10 of Kanagawa phenomenon-positive *V. parahaemolyticus* (positive controls) and uninoculated medium (negative control) were run concurrently whenever a batch of the culture filtrate of the test strains were assayed by the bead-ELISA. Haemolytic activity of the parent strain *V. cholerae* having the ATCC Accession No. 202010 with erythrocytes from rabbit, sheep, chicken and man was determined as described previously (ref. Nair G B, Oku Y, Takeda Y et al. Toxin profiles of *Vibrio cholerae* non-01 from environmental sources in Calcutta, India. Appl Environ Microbiol 1988; 54: 3180–3182). This strain was found not to have the toxin genes and not to have cholera toxin-like and other cytotoxin activities. The presence of the cryptic hemolysin A gene in this strain has been ascertained by hybridization with hlyA probe. This is essential since the integration of ctxB subunit gene has to be carried out by targeted recombination at hlyA locus. Since the product of tcpA gene is the main component of the pilus required for effective colonization of *Vibrio cholerae* in the intestine, its presence has also been ascertained by hybridization with tcpA probe. Further, since the transcriptional activator ToxR is required for the optimal expression of genes under the control of ctx promoter, the presence of the toxR gene has been ascertained by hybridization with the toxR probe.

Further, the *V. cholerae* strain having the ATCC Accession No. 202010 has been tested in a ligated ileal loop assay and RITARD model to ascertain whether it is reactogenic and whether it can colonize the intestine effectively. For the rabbit ileal loop assays, outbred New Zealand white rabbits of either sex weighing between 1.5 to 2.5 kg body weight were selected. Experimental animals were starved for 36 hours but were given water ad libitum. Surgery was done under anesthesia given intravenously. The ileal loop procedure was essentially similar to that described by S. N. De [De, S. N., Nature, 183, 1533–1534 (1959)]. The intestine was brought out through a midline incision. The selected small intestinal portion was washed carefully with warm (37° C.) sterile PBS (0.1 M, pH 7.4). A total of 8 loops were prepared in each rabbit. The length of the loop and the inter loop were 5 cms and 2 cms, respectively. One ml of live bacterial cell suspension containing about $10^8$ cells was introduced into each loop. *V. cholerae* 569B was used as the positive control and sterile PBS (0.01 M, pH 7.4) was used as the negative control. After inoculation, the small intestine of the animal was introduced carefully inside the open abdomen and then the incision was sutured. Animals were kept in their cages and supplied with water. Animals were sacrificed after 18 to 20 hours and an index of fluid accumulation (FA) was calculated from the ratio of loop fluid volume to loop length which was expressed as ml/cm. A test preparation was considered positive if the ratio was >0.9. Results were discarded if control reactions were inappropriate.

The *V. cholerae* strain having the ATCC Accession No. 202010 was tested twice in the ileum of two different rabbits. It did not cause any fluid accumulation. The strain having the ATCC Accession No. 202010 was tested for its ability to induce diarrhea and colonization in the RITARD model. Outbred New Zealand white rabbits of either sex weighing between 1.7 to 2.5 kg were selected for the colonization experiments. All of the animals were acclimatized in the laboratory for one week. The experimental rabbits were treated with a course of metronidazole (125 mg/rabbit/day) and sulfaquinoxaline sodium (464 mg/rabbit/day) repeated at an interval of two days, in order to clean the animal of intestinal protozoan pathogens such as Giardia and Coccidia. For preparing the oral inoculum, the strain having the ATCC Accession No. 202010 was grown overnight in tryptic soy broth (TSB, Difco, USA) at 37° C. for 18 hours in an orbital shaker. Cells were harvested by centrifugation at 8000 rpm for 15 minutes. The pellet was suspended in sterile phosphate buffered saline (pH 7.4) and the bacterial density was estimated in a spectrophotometer at 540 nm and diluted using PBS to an optical density of approximately $10^9$ cells.

For oral innoculation, rabbits were fasted for 36 hours but water was given adlibitum; 35 minutes before oral innoculation each rabbit was anesthetized intramuscularly with ketamine (35 mg/kg body weight) and 4 mg/kg body weight of xylazine. After 5 minutes, the rabbits were administered 50 mg of cimetidine which is a $H_2$ receptor blocker that inhibits the secretion of HCl from peptic cells of the stomach. After 15 minutes, a feeding tube (Accumark, Feeding Catheter, USA) was placed per os and 15 ml of a 5% solution of sodium bicarbonate (SRL India, sodium bicarbonate neutralizes HCl present in stomach) was introduced. At '0' time another 15 ml of 5% solution of sodium bicarbonate was given, followed immediately by the bacterial inoculum suspended in 15 ml of 0.01 M PBS (pH-7.4). After 30 minutes, 2 ml of tincture of opium was given intraperitoneally. The rabbits were then returned to the cages and given a limited amount of sterilized water and food. Diarrhea was scored according to a grading system using the following characteristics. Stools were graded as follows: grade 1 represents normal stool without diarrhea; grade 2 represents diarrhea with soft mushy stools, also termed as moderate diarrhea, and grade 3 represents diarrhea with catarrhal and watery diarrhea, being termed as severe diarrhea. The strain having the ATCC Accession No. 202011 does not cause diarrhea, showing it is not reactogenic. To study the colonization of the *V. cholerae* strain having the ATCC Accession No. 202011 after 18 hours following innoculation, the rabbits were anesthetized and their intestines were taken out after opening the abdomen surgically. Ten cm of the distal ileum was tied at both ends with umbilical tape (No.11) and cut. The 10 centimeter ileum was placed into a beaker containing 10 ml of sterile 0.01 M PBS (pH 7.4). The pieces of intestine were opened longitudinally and washed gently. Serial dilutions were prepared from the washed materials. The tissue portion of ileum was weighed and homogenized with 10 ml of PBS (0.01 M, pH 7.4) and homogenized. Serial dilutions of the homogenate was prepared. The rabbits were finally sacrificed using 2 ml of Euthanasia 6-solution 1 (Veterinary Lab./Inc. Kansas, USA) by intravenous injection. Neat and serial dilutions of the intestinal wash and homogenized material of ileum were plated on selective medium. The plates were incubated at 37° C. and colony counts were made 24 hours later using a colony counter and expressed as colony forming units. The *V. cholerae* strain having the ATCC Accession No. 202010 displayed impressive colonization ability. This is probably due to the presence of the toxin coregulated pilus whose presence was determined by hybridization.

The *V. cholerae* strain having the ATCC Accession No. 202010 can be grown in Luria broth at 37° C. temperature and stored in the same medium with 20% (vol/vol) glycerol at −70° C. This strain having the ATCC Accession No. 202010 has been used as parent strain for preparation of the cholera vaccine strain having the ATCC Accession No. 202011.

EXAMPLE 2

The vaccine strain of *Vibrio cholerae*, having the ATCC Accession No. 202010 has been constructed by integrating the gene encoding the B subunit of the cholera toxin into the chromosome of the parent strain having the ATCC Accession No. 202010. This has been achieved by targeted recombination, at the hlyA locus of the chromosome of the *V. cholerae* strain having ATCC Accession No. 202010. This briefly involves the following steps:

(i) Creation of a construct of ctxB subunit gene with its own Shine-Delgarno sequence and the promoter of ctx operon by first cloning the cholera toxin (ctx) operon from the chromosome of known *V. cholerae* 569B strain (National Institute of Cholera and Enteric Diseases) and then deleting the ctxA subunit gene from the cloned operon by inverse PCR.

(ii) Cloning of the target locus hemolysinA gene (hlyA) for the purpose of targeted recombination.

(iii) Disrupting the hlyA gene sequence by the ctxB subunit gene construct as obtained at step (i).

(iv) Cloning of the disrupted hlyA construct that has the ctxB subunit gene, into the suicide plasmid vector.

(v) Mobilization of the suicide vector, bearing the disrupted hlyA construct into the parent strain by conjugation, in order to allow targeted integration of the ctxB gene construct at the hlyA gene.

(vi) Identification of the recombinant *V. cholerae* clones with the integrated ctxB gene by Southern hybridization and polymerase chain reaction.

To facilitate the preparation of the vaccine using the parent strain, having ATCC Accession No. 202010, a series of genetic manipulations, leading to the preparation of ctxB subunit gene flanked by hlyA gene sequences, were carried out. The first step among the manipulations was to clone the ctx operon of *Vibrio cholerae*. The ctx operon of *Vibrio cholerae* strain 569B was cloned after its amplification from the genome by polymerase chain reaction. For the amplification of ctx operon, the following primers were used: Oligonucleotide CT1 is complementary to the chromosomal DNA sequence located 149–172 nucleotides upstream of the transcription start site of ctx operon, Oligonucleotide CT2 is complementary to the chromosomal DNA sequence located 43–67 nucleotides downstream of the stop codon of ctx. When these two oligonucleotides were used as primers to amplify the DNA sequence, the product was the complete ctx operon consisting of the genes encoding cholera toxin A and B subunits along with the promoter and the upstream ToxR binding repeats at the 5' end, and the transcription termination signal at the 3' end of the operon.

In the polymerase chain reaction 100 ng of the known *Vibrio cholerae* 569B chromosomal DNA was used as template to amplify the ctx operon with 1.0 μM of the primers CT1 and CT2. Following an initial denaturation step at 97° C. for 2 minutes, the reaction was cycled 30 times through a denaturation step at 94° C. for 1 minute, annealing step at 62° C. for 1 minute and extension step at 72° C. for 2 minutes. At the end of the last cycle, an additional extension step was included for 10 minutes at 72° C. After the polymerase chain reaction, the reaction mix was extracted with equal volume of a 50:50 mixture of phenol:chloroform. The aqueous phase was passed through Sephadex G50 spin column to remove free nucleotides and precipitated by ethanol. The DNA was resuspended and treated with T4 DNA polymerase enzyme in the presence of 200 μM dTTP. This resulted in the amplified DNA product with 5' TT-dinucleotide overhangs. To clone the amplified DNA that was modified as above, the plasmid vector pBS+ was first linearized with EcoRI restriction enzyme. It was then treated with the Klenow fragment of *E. coli* DNA polymerase I in the presence of 200 μM dATP. This treatment resulted in 5' AA overhangs at both ends of the linearized pBS+ vector DNA. This vector DNA preparation was ligated to the amplified ctx operon with 5' TT-overhangs at 1:2 molar ratio by T4 DNA ligase. After this ligation reaction, the resulting mix was used to transform *E. coli* "Sure" strain by electroporation. The resulting recombinant plasmid clones were analyzed by restriction enzymes for which the sites on the ctx operon were known (e.g. Nde I, XbaI, ClaI). The insert of one clone called pGT1 had the complete ctx operon as confirmed by restriction analysis and sequencing. The nucleotide sequence of the complete B subunit gene was determined in order to rule out the possibility of any error introduced during the polymerase chain reaction. This plasmid clone pGT1 was used in the subsequent step.

In the next step, deletion of complete ctx-A coding sequence from the plasmid clone pGT1 was achieved by inverse polymerase chain reaction using oligonucleotide primers that diverge from each other and amplify the plasmid excluding the ctx-A gene. Oligonucleotide CT3 (SEQ ID NO: 3) is complementary to the chromosomal DNA sequence located +9 to −21 nucleotides with respect to the transcription start site of the ctx operon. Oligonucleotide CT4 (SEQ ID NO: 4) is located −16 to +15 nucleotides with respect to the first base of the initiation codon of the ctx B gene. The oligonucleotides CT3 and CT4 were phosphorylated at their 5' ends by T4 polynucleotide kinase. An inverse polymerase chain reaction is carried out using the phosphorylated oligonucleotides CT3 and CT4 as primers and the plasmid pGT1 as the template DNA.

The resulting amplified product which was 3.8 kilobase in size, is phenolyzed, passed through Sephadex G-50 spin column to remove the free nucleotides and ethanol precipitated. It was then treated with T4 DNA polymerase in the presence of 200 μM dTTP to generate 5' GG-overhangs at the terminus corresponding to CT3 and 5' CC-overhangs at the terminus corresponding to CT4. Ligation of the complimentary termini was carried out by T4 DNA ligase at a final concentration of 2 ng/μl of the DNA in the ligation mix, to facilitate intramolecular ligation. The ligation product was used to transform *E. coli* "Sure" strain by electroporation. The recircularization of the inverse polymerase chain reaction product resulted in the fusion of the ctx promoter and the ctx B subunit gene. This construct ctx Promoter-B was identified in the various plasmid clones by polymerase chain reaction using CT1 and CT2 as primers. The product yielded was a 0.63 kilobase fragment corresponding to the ctx Promoter-B construct.

The expression of B subunit from the various clones was confirmed by Bead ELISA assay. The nucleotide sequence of the ctx-Promoter-B construct of one plasmid clone pGT 3.1 was determined in order to confirm the sequence at the promoter-B subunit gene fusion point. This confirmed the fusion of the ctx operon promoter and the ToxR binding repeats with the ctxB subunit gene containing its own Shine-Delgarno sequence. The ctxB gene exhibited a theoretically perfect Shine-Delgarno sequence (TAA GGA) and there is evidence in the literature that the ctxB ribosome binding site is about nine fold more efficient than the ctxA site. (J. J. Mekalanos, D. J. Swartz G. D. N. Pearson, Nitarford, I. Groyne & Michel de Wilde (1983) Nature 306, 551–557). The ctx Promoter-B gene construct from pGT3.1 was used in a latter step to disrupt cloned hlyA gene.

Since it was decided to introduce the ctx Promoter-B gene construct into the *Vibrio cholerae* strain having the ATCC Accession No. 20210 by targeted recombination at the hlyA gene, it was essential to make a construct in which cloned hlyA gene sequence is disrupted in the middle by the ctx Promoter-B construct. For this purpose, it was necessary to clone the hlyA gene of *V. cholerae*. A partial hlyA gene sequence which lacks the 5' flanking region and a large part of the coding region at the 3' side was cloned after its amplifcation from the *Vibrio cholerae* genome. For the amplification, the following oligo nucleotide primers were used: Oligo nucleotide HA1 (SEQ ID NO: 5) is complementary to the chromosomal DNA sequence located between −19 to +6 nucleotides with respect to the start codon of the hlyA gene, and oligonucleotide HA2 (SEQ ID NO: 6) is complementary to the chromosomal DNA sequence located between 1714–1690 nucleotides from the start codon of the hlyA gene. The size of the complete coding region of hlyA gene is about 2.2 kilobases, out of which 1.7 kilobase of the hlyA gene was amplified from the genomic DNA of *V. cholerae* 01 strain. After an initial denaturation step at 97° C. for 2 minutes, the reaction was cycled 30 times through a denaturation step at 94° C. for 1 minute, an annealing step at 62° C. for 1 minute and an extension step at 72° C. for 2 minutes. At the end of the last cycle, an additional extension step was included at 72° C. for 10 minutes. The polymerase chain reaction product was analyzed by agarose gel electrophoresis for the presence of a 1.7 kilobase DNA fragment. The reaction product was phenolyzed, passed through Sephadex G-50 spin column to remove free nucleotides and ethanol precipitated. The purified DNA was treated with T4 DNA polymerase in the presence of 200 μM dGTP to generate 5' TT-overhangs at the termini. To clone the amplified hlyA gene sequence with the modified termini as above, the plasmid vector pUC9 was first linearized with the restriction enzyme EcoRI. The linearized pUC9 DNA was then treated with Klenow fragment of *E. coli* DNA polymerase I in the presence of 200 μM dATP to generate 5' AA-overhangs at the termini. This vector DNA preparation was ligated to the amplified hlyA gene sequence with 5' TT overhangs at 1:2 molar ratio by T4 DNA ligase. Following ligation, the reaction mix was used to transform *E. coli* "Sure" strain by electroporation. The resulting plasmid clones were analyzed by digestion with EcoRI and HpaI restriction enzymes. The 1.7 kilobase EcoRI insert should have 2 HpaI sites in the middle region separated by a 0.4 kilobase sequence. One of the plasmid clones pGT89 which had the 1.7 kilobase hlyA insert was used in the subsequent step to disrupt the hlyA sequence by the ctx promoter-B gene construct.

In the next step, the ctx Promoter-B construct of pGT 3.1 was amplified, using the oligonucleotide primers CT1 and CT2. The amplified product was phenolyzed, passed through Sephadex G50 spin column and ethanol precipitated. The purified ctx Promoter-B construct fragment was treated with T4 DNA polymerase in the presence of dTTP to generate 5' TT-overhangs at the termini. The ctx Promoter-B construct with 5' TT-overhangs had to be inserted into the middle of the cloned hlyA gene sequence in place of the 0.4 kilobase HpaI fragment. Since the plasmid vector pUC9 does not have a site for HpaI enzyme, digestion of pGT89 with HpaI should result in a 0.4 kilobase fragment from the middle of the cloned hlyA gene sequence and a 3.9 kilobase fragment. pGT89 was digested with HpaI enzyme and the DNA fragments were separated by agarose gel electrophoresis. The 3.9 kilobase HpaI fragment was electroeluted and purified. It was then treated with T4 DNA polymerase in the presence of dGTP to generate 5' AA-overhangs. The 3.9 kilobase fragment with 5' AA-overhangs was ligated to the ctx Pr-B construct with T4 DNA ligase. The ligated mix was used to transform $E.$ $coli$ "Sure" strain by electroporation. The recombinant plasmid clones were identified by colony hybridization using a ctx Promoter-B Construct as the probe. Digestion of the recombinant plasmids with EcoRI enzyme resulted in a 1.9 kilobase insert of hlyA gene sequence disrupted in the middle by the ctx Promoter-B construct. The EcoRI insert from the recombinant plasmid pGT 39 was cloned into the suicide vector pGP704. The nucleotide sequences of the ctx Promoter-B construct along with the flanking hlyA sequences of pGT39 were determined.

In the next step, the ctx promoter-B construct along with the flanking hlyA sequences, were cloned into the plasmid suicide vector. The plasmid suicide vector pGP704 was digested with EcoRI enzyme and the 5' phosphate groups of the linearized vector were removed by treatment with calf intestinal phosphatase. The EcoRI digested, dephosphorylated pGP704 was electrophoresed on a 0.8% agarose gel and the corresponding DNA band was electroeluted and purified. This was done to make sure that no trace of the undigested vector DNA was present in the vector DNA preparation. The vector was then ligated to the 1.9 kilobase EcoRI insert of pGT39 at 1:5 molar ratio by T4 DNA ligase, and the ligated mix was used to transform *E. coli* SM10 pir strain by electroporation. The recombinant plasmid clones were identified by colony hybridization, using a ctx Promoter-B construct as the probe. Digestion of the recombinant plasmid with EcoRI gave a 1.9 kilobase insert which represented the cloned hlyA gene sequence disrupted by the ctx Promoter-B construct. One of the clones pGT27 was used for mobilization into the *V. cholerae* strain having the ATCC Accession No. 202010 for integration at the hlyA gene.

In the following step, mobilization of pGT27 into parent *V. cholerae* strain having the ATCC Accession No. 202010 was achieved by conjugation between the *Vibrio cholerae* strain having the ATCC Accession No. 202010 and the *E. coli* strain SM10 pir containing the plasmid pGT27. The plasmid clone pGT27 in the *E. coli* host strain SM10 pir and the *V. cholerae* strain having the ATCC Accession No. 202010 were grown in Luria broth to midlog phase without shaking at 37° C. 0.5 ml of the *E. coli* donor strain and 0.5 ml of the *V. cholerae* recipient strain were mixed in 1.5 ml microfuge tubes and briefly centrifuged at 6000 rpm for 1 minute to collect the cells at the bottom. After removing the supernatant 50 $\mu$l volume of Luria broth was added to cell pellet and the cells are suspended in it by pipetting up and down. The cell suspension was then spotted on a 0.4 mm membrane disc placed on the surface of a LB agar medium.

After the suspension was absorbed on the membrane, the donor and the recipient cells were allowed to mate at 37° C. for 4 hours. The membrane filter was then collected into a 5 ml screwcap tube and 1 ml of LB medium was added. The cells on the membrane were resuspended in the medium by vortexing briefly. 10 $\mu$l of the cell suspension was spread on LB agar medium containing 10 $\mu$g/ml of streptomycin sulfate and 100 $\mu$g/ml of ampicillin. At such a high concentration of ampicillin, it is expected that the plasmid pGT27, which confers the ampicillin resistance, would be repeated in tandem at a relatively higher frequency, and therefore selected from this drug pressure.

The ampicillin resistant colonies were analysed by hybridization with ctxB gene probe. The chromosomal preparations DNA from the recombinant clones that hybridized with the probe, were used as template in polymerase chain reaction with the hly A specific primers HA1 and HA2. Both the 1.7 kilobase and the 1.9 kilobase fragments were amplified from all the clones. When two different size fragments, as defined by the same set of primers in this case, were present in a single copy, then the smaller fragment is usually preferentially amplified in the polymerase chain reaction. This phenonemon is reflected in their band intensities when examined by agarose gel electrophoresis. If the larger one is present in multiple copies, then the amount of the larger fragment amplified would be much more than when it was present as a single copy.

One clone was found to have more intense 1.9 kilobase fragment than the 1.7 kilobase band and secretes more of B subunit than several other clones as determined by bead ELISA. This clone having the ATCC Accession No. 202011 was subcultured in LB medium containing 10 $\mu$g/ml of streptomycin sulfate for about 20 generations. The cells from this culture were plated on LB plate containing 10 $\mu$g/ml of streptomycin sulfate and the colonies obtained were hybridized with the ctxB gene probe. All colonies hybridized indicated the stability of the integrated pGT27 even after 20 generations. Genomic DNA from the recombinant *V. cholerae* clone having the ATCC Accession No. 202011 was isolated and digested with XbaI, SalI and HpaI restriction enzymes separately. The Southern blot of the above digestions was hybridized with ctxB probe and hlyA probes in separate experiments.

Cholera vaccine having the ATCC Accession No. 202011 was passaged (subcultured) in LB medium 56 times without any drug, each passage representing about 20 generations. About 1500 single colonies were checked for presence of ctxB hybridization with the ctx Pr-B construct fragment as the probe. All of the colonies showed positive hybridization with the probe indicating that ctx Pr-B construct was stably maintained even after about $\geqq$1000 generations of growth in the absence of ampicillin.

*V. cholerae* having the ATCC Accession No. 202011 was chosen as vaccine strain. It was tested by Rabbit ileal loop assay to determine whether it is reactogenic. Outbred New Zealand white rabbits of either sex weighing between 1.5 to 2.5 kg body weight were selected for rabbit ileal loop assays. Experimental animals were starved for 36 hours but were given water ad libitum. Surgery was done under anesthesia given intravenously. The ileal loop procedure was essentially similar to that described by S. N. De [De, S. N., Nature, 183, 1533–1534 (1959)]. The intestine was brought out through a midline incision. The selected small intestinal portion were washed carefully with warm (37° C.) sterile PBS (0.1 M, pH 7.4). A total of 8 loops were prepared in each rabbit. The length of the loop and the inter loop were 5 cms and 2 cms, respectively. One ml of live bacterial cell suspension containing about $10^8$ cells was then introduced in each loop. The known *V. cholerae* 569B was used as the positive control and sterile PBS (0.01 M, pH 7.4) was used as the negative control. After inoculation, the small intestine of the animal was introduced carefully inside the open abdomen and then the incision was sutured. Animals were kept in their cages and supplied with water. Animals were sacrificed after 18 to 20 hours and an index of fluid accumulation (FA) was calculated from the ratio of loop fluid volume to loop length which is expressed as ml/cm. A test preparation was considered positive if the ratio was >0.9. Results were discarded if control reactions were inappropriate. The vaccine strain having the ATCC Accession No. 202011 was tested twice in the ileum of two different rabbits. The vaccine strain having the ATCC Accession No. 202011 did not induce fluid accumulation. This attested the fact that the vaccine construct produces the B subunit but as is expected, is innocuous and incapable of inducing fluid accumulation.

The next series of experiments were conducted to determine the colonization ability and protective ability of the vaccine using an in vivo rabbit model. For this purpose, outbred new Zealand white rabbits of either sex weighing between 1.7 to 2.5 kg were selected for the colonization experiments. All of the animals were acclimatized in the laboratory for a week. The experimental rabbits were treated with a course of metronidazole (125 mg/rabbit/day) and sulfaquinoxaline sodium (464 mg/rabbit/day) and this course was repeated at an interval of two days to clean the animal of intestinal protozoan pathogens like Giardia and Coccidia.

For preparing the oral inoculum the vaccine strain having the ATCC Accession No. 202011 was grown overnight in tryptic soy broth (TSB, Difco, USA) at 37° C. for 18 hours in an orbital shaker. Cells were harvested by centrifugation at 8000 rpm for 15 minutes. The pellet was suspended in sterile phosphate buffered saline (pH 7.4) and the bacterial density was estimated in a spectrophotometer at 540 nm and diluted using PBS to an optical density of approximately $10^9$ cells.

Before oral immunization, rabbits were fasted for 36 hours but water was given adlibitum; 35 minutes before oral inoculation each rabbit was anesthetized intramuscularly with ketamine (35 mg/kg body weight) and 4 mg/kg body weight of xylazine. After 5 minutes, the rabbits were administered 50 mg of cimetidine which is a $H_2$ receptor blocker and inhibits the secretion of HCl from peptic cells of the stomach. After 15 minutes, a feeding tube (Accumark, Feeding Catheter, USA) was placed per os and 15 ml of a 5% solution of sodium bicarbonate (SRL India, sodium bicarbonate neutralizes HCl present in stomach) was introduced. At '0' time another 15 ml of 5% solution of sodium bicarbonate was given followed immediately by the bacterial inoculum suspended in 15 ml of 0.01 M PBS (pH-7.4). After 30 minutes, 2 ml of tincture of opium was given intraperitoneally. The rabbits were then returned to the cages and given limited amount of sterilized water and food. Both the experimental and control groups of rabbits were orally immunized with the vaccine strain having the ATCC Accession No. 202011 on day 0, day 7 and day 14. The control group was treated with uninoculated 15 ml of Tryptic soy broth (Difco, USA). On day 21 of the experiment, all the immunized animals were challenged by homologous or heterologous strains to determine the extent of protection. The ability of the animals to survive the challenge as well as the colonization ability of the organisms was studied.

To study, the colonization of the test strains including the vaccine strain, the experimental rabbits were sacrificed after 18 hours of inoculation. The rabbits were anesthetized and the intestine was taken out after opening the abdomen surgically. Ten cm of the distal ileum was tied at both ends with umbilical tape (No.11) and cut. The 10 centimeter ileum was placed into a beaker containing 10 ml of sterile 0.01 M PBS (pH 7.4). The pieces of intestine were opened longitudinally and washed gently. Serial dilutions were prepared from the washed materials. The tissue portion of ileum was weighed and homogenized with 10 ml of PBS (0.01 M, pH 7.4) and homogenized. Serial dilutions of the homogenate was prepared. The rabbits were finally sacrificed using 2 ml of Euthanasia 6-solution 1 (Veterinary Lab./Inc. Kansas, USA) by intravenous injection. Neat and serial dilutions of the intestinal wash and homogenized material of ileum was plated on selective medium. The plates were incubated at 37° C. and colony counts were made 24 hours later using a colony counter and expressed as colony forming units.

Homologous challenge studies were done with the same strain thas was used for immunization and challenge. Conversely, heterologous challenge studies were done with different strains used for immunization and challenge. Heterologous strains were chosen to represent both the biotypes (E1 Tor and classical) of *V. cholerae*.

Immunized rabbits challenged with homologous and heterologous strains were observed for clinical signs of diarrhea. Diarrhea was scored according to a grading system using the following characteristics. Grade 1 represents normal stool without diarrhea; grade 2 represents diarrhea with soft mushy stools also termed as moderate diarrhea and grade 3 represents diarrhea with catarrhal and watery diarrhea being termed as severe diarrhea. It was clearly observed that the vaccine strain having the ATCC Acceession No. 202011 did not induce diarrhea when fed orally to rabbits. Based on these results, challenge studies with parent strains of *V. cholerae* of 01 serotype and of both biotypes E1 Tor and classical were conduced in several batches. The data can be summarized as follows:

1. Rabbit immunized with vaccine strain having the ATCC Accession No. 202011 were significantly protected from a challenge with a classical biotype and an E1 Tor biotype strain. This was evident from the absence of diarrhea in the immunized rabbits while the control rabbits had profound diarrhea.
2. The colonization ability of the challenge strains in the immunized rabbits were significantly lower as compared to the control rabbits.
3. The non-rectogenicity of the vaccine strain having the ATCC Accession No. 202011 was again evident by its inability to provoke diarrhea in the control rabbits.
4. The vaccine strain having the ATCC Accession No. 202011 is immunogenic as there was a significant rise in antibody titre against lipopolysaccharide, outer membrane protein, whole cell lysate and cholera toxin in immune sera as compared to the preimune sera of rabbits orally immunized with the vaccine strain.

In summary then *V. cholerae* strain having ATCC Accession No. 202011 is a candidate cholera vaccine strain which is devoid of all known virulence genes, is non-reactogenic in an animal model, elaborates the immunogenic "B" subunit of the cholera toxin and is capable of affording full protection against both biotypes of *V. cholerae*, E1 Tor and classical, in a RITARD model. The cholerae vaccine having the ATCC Accession No. 202011 can be grown in Luria broth containing 50 $\mu$g/ml of ampicillin at 37° C. temperature and stored in the same medium with 20% (Vol/Vol) glycerol at -70° C.

The examples illustrated above should not be construed to limit the scope of the present invention.

---

What is claimed is:

1. An isolated *Vibrio cholerae* strain deposited as Accession No. ATCC 202011.

2. An isolated *Vibrio cholerae* strain deposited as Accession No. ATCC 202010.

3. A vaccine for cholera, prepared from an isolated *Vibrio cholerae* strain deposited as Accession No. ATCC 202010.

4. A process for the preparation of a chlorea vaccine, comprising:

(A) Creating a first recombinant plasmid clone comprising a ctx operon, from a toxic strain of *Vibrio cholerae*, and subsequently deleting the ctx A gene from said operon by inverse PCR, (B) Creating a second recombinant plasmid clone comprising a hly A gene from *Vibrio cholerae* and the plasmid insert of (A) by amplifying the plasmid insert of (A), and inserting the amplification product in place of the 0.4 kilobase Hpa I restriction fragment, (C) Transforming a *Vibrio cholerae* strain having the ATCC Accession No. 202010 by cloning the insert of (B) into a plasmid suicide vector and transforming *Eschericia coli* with said recombinant suicide vector, and conjugating the transformed *Eschericia coli* with *V. cholerae* strain ATCC 202010.

5. A vaccine for cholera prepared by the process of claim 4.

6. A *Vibrio cholerae* strain, comprising a hemolysin A (hly A) gene, a toxin coregulated pilus A (tcp A) gene, and a toxR gene but not a gene encoding cholera toxin, a gene encoding a zonula occludens toxin, or a gene encoding an accessory cholera enterotoxin.

7. A process for the preparation of a cholera vaccine, comprising:

(A) Creating a first recombinant plasmid clone comprising a ctx operon, from a toxic strain of *Vibrio cholerae*, and subsequently deleting the ctx A gene from said operon by inverse PCR, (B) Creating a second recombinant plasmid clone comprising a hly A gene from *Vibrio cholerae* and the plasmid insert of (A) by amplifying the plasmid insert of (A), and inserting the amplification product in place of the 0.4 kilobase Hpa I restriction fragment, (C) Transforming a *Vibrio cholerae* strain of claim 6, by cloning the insert of (B) into a plasmid suicide vector and transforming *Eschericia coli* with said recombinant suicide vector, and conjugating the transformed *Eschericia coli* with said *Vibrio cholerae* strain of claim 6.

* * * * *